United States Patent [19]

Gates

[11] 4,001,003
[45] Jan. 4, 1977

[54] PLANT PHYSIOLOGICALLY ACTIVE COMPOSITIONS CONTAINING 2-HALO-2,3-DIHYDROBENZOFURAN-5-OLESTERS OF SULFONIC ACIDS AND METHODS OF USE

[75] Inventor: Peter Stuart Gates, Cambridge, England

[73] Assignee: Fisons Limited, London, England

[22] Filed: Apr. 16, 1975

[21] Appl. No.: 568,582

Related U.S. Application Data

[62] Division of Ser. No. 460,150, April 11, 1974, Pat. No. 3,896,151.

[30] Foreign Application Priority Data

Apr. 17, 1973 United Kingdom ............ 18395/73

[52] U.S. Cl. .................................................. 71/88
[51] Int. Cl.² ........................................... A01N 9/00
[58] Field of Search ........................................ 71/88

[56] References Cited

UNITED STATES PATENTS

| | | | |
|---|---|---|---|
| 3,689,507 | 9/1972 | Gates et al. | 71/88 X |
| 3,861,900 | 1/1975 | Fischer | 71/88 |
| 3,898,072 | 8/1975 | Fischer | 71/88 |

*Primary Examiner*—Joseph Paul Brust
*Attorney, Agent, or Firm*—Wenderoth, Lind & Ponack

[57] ABSTRACT

A plant physiologically active composition containing as the active ingredient a compound of formula

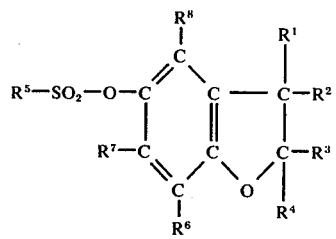

characterized in that $R^1$, $R^2$ and $R^3$ are the same or different and each represents hydrogen or alkyl, or $R^1$ and $R^2$ together or $R^2$ and $R^3$ together form an alkylene chain;

$R^4$ represents a halogen atom;

$R^5$ represents alkyl, substituted alkyl, aryl or substituted aryl; and $R^6$, $R^7$ and $R^8$ are the same or different and each represents hydrogen, alkyl, halogen, cyano, alkanoyl or alkoxy. The present invention also involves methods of using the aforementioned compositions.

29 Claims, No Drawings

PLANT PHYSIOLOGICALLY ACTIVE COMPOSITIONS CONTAINING 2-HALO-2,3-DIHYDROBENZOFURAN-5-OL ESTERS OF SULFONIC ACIDS AND METHODS OF USE

This is a division of application Ser. No. 460,150 filed Apr. 11, 1974, now U.S. Pat. No. 3,896,151 issued July 22, 1975.

The present invention relates to new compounds, their preparation, their plant use, their use as intermediates and plant physiologically active compositions containing them.

The invention provides a compound of formula:

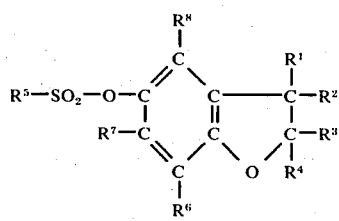

I in which $R^1$, $R^2$ and $R^3$ are the same or different and each represents hydrogen or alkyl (for example of 1 to 6 carbon atoms, such as methyl or ethyl), or $R^1$ and $R^2$ together or $R^2$ and $R^3$ together form an alkylene chain (for example of 2–5 carbon atoms);

$R^4$ represents a halogen (fluorine, chlorine, bromine or iodine) atom;

$R^5$ represents alkyl (for example of 1–4 carbon atoms such as methyl or ethyl), substituted alkyl (for example of 1–4 carbon atoms substituted by halogen or alkoxy of 1–6 carbon atoms such as chloromethyl, methoxypropyl and bromoethyl), aryl (for example phenyl) or substituted aryl (for example substituted by halogen or alkyl of 1–4 carbon atoms such as chlorophenyl or tolyl); and $R^6$, $R^7$ and $R^8$ are the same or different and each represents hydrogen, alkyl (for example of 1 to 4 carbon atoms, such as methyl, ethyl or isopropyl), halogen (for example chlorine or bromine), cyano, alkanoyl (for example of 2 to 6 carbon atoms, such as acetyl) or alkoxy (for example of 1–4 carbon atoms, such as methoxy).

The invention provides also a process for preparing the compound in which $R^4$ represents a chlorine, bromine or iodine atom, which process comprises replacing the 2-hydroxy group of the corresponding 2-hydroxy compound by a chlorine, bromine or iodine atom respectively.

The invention also provides a process for preparing the compound in which $R^4$ represents a fluorine, bromine or iodine atom, which process comprises reacting the corresponding compound in which $R^4$ represents a chlorine atom with a metal fluoride, bromide or iodide respectively.

The invention also provides a method of combating weeds at a locus infested or liable to be infested by them, which method comprises applying to the locus a weed-combating amount of the compound.

The invention provides in addition a method of regulating the growth of a plant, which method comprises applying to the locus at which the plant is growing or is to grow a plant growth regulant amount of the compound.

In addition, the invention provides a plant physiologically active composition containing the compound, especially a plant physiologically active composition comprising the compound together with at least one material selected from carriers, surface active agents, other pesticides and other plant growth regulants.

The invention further provides a process for preparing a compound of formula I in which $R^4$ represents alkoxy and $R^1$, $R^2$, $R^3$, $R^5$, $R^6$, $R^7$ and $R^8$ are as defined above, which process comprises reacting the present compound with an alkanol.

In a particular embodiment, $R^1$ and $R^2$ represent alkyl radicals (e.g. of 1–6 carbon atoms), for example the same alkyl radical, e.g. each represents a methyl group.

$R^3$ preferably represents a hydrogen atom.

$R^4$ may for example represent a chlorine or bromine, especially a chlorine, atom.

In a preferred embodiment, $R^6$, $R^7$ and $R^8$ represent a hydrogen atom.

$R^5$ may for example represent an alkyl group of 1–4 carbon atoms, especially methyl.

The present compounds can be prepared in ways which are known in themselves. Thus, the compounds in which $R^4$ represents a chlorine, bromine or iodine atom may be prepared by replacing the 2-hydroxy group of the corresponding 2-hydroxy compound by a chlorine, bromine or iodine atom respectively. The compound in which $R^4$ represents a chlorine or bromine atom is preferably prepared by reacting the 2-hydroxy compound, in the presence of a tertiary base, with thionyl chloride or thionyl bromide respectively. The tertiary amine can be for example pyridine, triethylamine or N,N-dimethylaniline, particularly pyridine. The reaction is normally carried out in a solvent such as methylene chloride and normally without heating. The present compound in which $R^4$ represents a chlorine atom may alternatively be prepared by reacting the corresponding compound in which $R^4$ represents hydroxy with phosphorus pentachloride, phosphorus trichloride, phosphorus oxychloride, phosgene, or triphenylphosphine and carbon tetrachloride; the present compound in which $R^4$ represents a bromine atom may be prepared analogously. The present compound in which $R^4$ represents an iodine atom may be prepared by reacting the corresponding compound in which $R^4$ represents hydroxy with phosphoric acid and an iodide which is potassium or sodium iodide.

The present compounds are useful intermediates. In particular they may surprisingly be reacted with alkanols to form the corresponding 2-alkoxy compounds. These 2-alkoxy compounds (e.g. those in which the alkoxy group contains 1–8 carbon atoms) are known herbicides — see our United Kingdom specification 1271659. The reaction is preferably conducted with heating.

The present compounds are active on plant physiology, affecting the growth of plants so that the compounds may be used as herbicides or plant growth regulants. The plant physiologically active compositions can be prepared by admixing the ingredients. Usually the compositions are initially produced in the form of concentrates, e.g. containing 0.5–85% of the present compound, and these are diluted with water or hydrocarbon, usually water, for application, generally such that the concentration of the compound is 0.05–5%. Percentages and parts in this specification are by weight unless otherwise indicated.

The compositions normally contain a surface active agent and/or a carrier.

The carrier may be a liquid, e.g. water (e.g. water used to dilute a concentrate for application). If water is employed as carrier in concentrate, an organic solvent may also be present as carrier, though this is not usually employed. A surface active agent may advantageously be present.

The carrier may be a liquid other than water, for example an organic solvent, usually a water-immiscible solvent, e.g. a hydrocarbon which boils within the range 130°–270° C, in which the compound is dissolved or suspended. A concentrate containing an organic solvent suitably also contains a surface active agent so that the concentrate acts as a self-emulsifiable oil on admixture with water.

The carrier may be a solid, which may be finely divided. Examples of suitable solids are clays, sand, mica, chalk, attapulgite, diatomite, perlite and sepiolite, and synthetic solid carriers, e.g. silicas, silicates and lignosulphonates Wettable powders soluble or dispersable in water may be formed by admixing the compound with or without a carrier with a surface active agent, and preferably micronising or pulverising.

Thus the present composition can for example be solid (e.g. dust or granules) and contain a solid carrier or liquid (e.g. an emulsifiable concentrate) and contain a liquid carrier which is a hydrocarbon which boils within the range 130°–270° C.

The term 'surface active agent' is used in the broad sense to include materials variously called emulsifying agents, dispersing agents and wetting agents. Such agents are well known in the art.

The surface active agents used may comprise anionic surface active agents, for example soaps, fatty sulphate esters such as dodecyl sodium sulphate, octadecyl sodium sulphate and cetyl-benzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise nonionic agents, for example condensation products of fatty acides, fatty alcohols or fatty substituted phenols with ethylene oxide, or fatty esters and ethers of sugars or polyhydric alcohols, or the products obtained from the latter by condensation with ethylene oxide, or the products known as block copolymers of ethylene oxide and propylene oxide.

The surface active agents may also comprise cationic agents, for example cetyl trimethylammonium bromide.

Preferred surface active agents include fatty alkyl sulphates, alkyl aryl sulphonates, fatty alkyl ethoxylates, sulphonated fatty alkyl ethoxylates, dialkyl sulphosuccinate esters, lignin sulphonate salts, sulphonated naphthaleneformaldehyde condensates and sulphonated urea-formaldehyde condensates.

The present active compound may be admixed with another pesticide, e.g. herbicide, insecticide or fungicide, or with another plant growth regulant or with a fertilizer. Particular advantages are obtained with mixtures with a second herbicide. The present compound may be used sequentially with a second herbicide, e.g. one herbicide applied before planting or before emergence of a crop and the other herbicide applied after emergence of the crop.

The second herbicide may be for example a phenoxyaliphatic acid, substituted urea, triazine, phenol, nitrile, bipyridylium compound, substituted benzoic acid, halogenated aliphatic acid, carbamate, thiocarbamate, chloroacetamide, diazine or arsenic herbicide. In respect of selective herbicidal compositions for post-emergence use, the second herbicide may be for example a substituted phenoxaliphatic acid; in respect of selective herbicidal compositions for pre-emergence use, the second herbicide may be for example a substituted urea or triazine; in respect of sequential selective herbicidal use, the second herbicide may be for example methyl 3-(m-tolylcarbamoyloxy) phenylcarbamate applied after emergence of the crop.

The phenoxyliphatic acid generally comprises alkyl and/or halogen substituted phenoxyaliphatic acids, and their salts, for example alkali metal, amine and alkanolamine salts, and functional derivatives, for example esters and amides. These compounds may be of activity such that they are recognised as commercial herbicides, or may be of only slight herbicidal activity. Examples of the substituted phenoxyaliphatic acids which may be mentioned include 2,4-dichlorophenoxyacetic acid, 2-methyl-4-chlorophenoxyacetic acid, 2,4,5-trichlorophenoxyacetic acid, gamma-2,4-dichlorophenoxybutyric acid, gamma-2-methyl-4-chlorophenoxy-butyric acid and alpha-2-methyl-4-chlorophenoxy-propionic acid.

The substituted urea generally comprises a tri- or tetrasubstituted urea such as N'-parachlorophenyl-N,N-dimethylurea, N-butyl-N'-(3,4-dichlorophenyl)-N-methylurea, N'-parachlorophenyl-O,N,N-trimethylisourea, N'-p-chlorophenyl-N-methoxy-N-methylurea, N,N-dimethyl-N'-phenylurea or 3-(4-bromophenyl)-1-methoxy-1-methylurea, or 1-(2-benzothiazolyl)-3-methylurea.

The triazine herbicide generally comprises a compound of the formula:

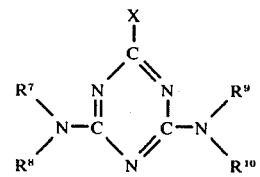

where X is a halogen, OY group or SY group, where Y is an alkyl group, and $R^7$, $R^8$, $R^9$ and $R^{10}$ are hydrogen or alkyl, such as 2-chloro-4,6-bisethylamino-1,3,5-triazine, 2-chloro-6-ethylamino-4-isopropylamino-1,3,5-triazine or 2,4-bis(isopropylamino)-6-methylthio-1,3,5-triazine.

The phenol herbicide generally comprises 4,6-dinitro-o-cresol or pentachlorophenol. The nitrile herbicide generally comprises 3,5-diiodo-4-hydroxy-benzonitrile, 3,5-dibromo-4-hydroxybenzonitrile or 2,6-dichlorobenzonitrile. The bipyridylium herbicide generally comprises 1,1'-dimethyl-4,4'-bipyridylium dichloride or 1,1'-ethylene-2,2'-bipyridylium dibromide. The substituted benzoic acid herbicide generally comprises 2,3,6-trichlorobenzoic acid, 2-methoxy-3,6-dichlorobenzoic acid or N-(1,1-dimethylpropyl)-3,5-dichlorobenzamide. The halogenated aliphatic acid herbicide generally comprises trichloroacetic acid or 2,2-dichloropropionic acid. The carbamate herbicide generally comprises isopropyl N-(3-chlorophenyl) carbamate, 4-chloro-2-butyl N-(3-chlorophenyl) carbamate, methyl 3-(m-tolylcarbamoyloxy)phenylcarbamate or D-N-ethyl-2-(phenylcarbanoyloxy)propionamide. The thiocarbamate herbicide generally comprises S-ethyl N,N-dipropylthio-carbamate, S-ethyl N,N-diisobutylthiocarbamate, S-(2,3-dichloroallyl) N,N-diisopropylthiocarbamate, S-ethyl-N-ethyl-N-cyclohexylthiocarbamate, S-propyl butylethylthiocarbamate or S-(2,3,3-trichloroallyl) N,N-diisopropylthiocarbamate. The chloroacetamide herbicide generally comprises N,N-diallyl-2-chloroacetamide or N-isopropyl-2-chloroacetanilide. The diazine herbicide generally comprises 5-bromo-6-methyl-3-sec-butyluracil, 3-cyclohexyl-5,6-trimethyleneuracil, 5-amino-4-chloro-2-phenyl-3-pyridazinone or 1,2-dihydropyridazine-3,6-dione. The arsenic herbicide generally comprises a salt of methane arsonic acid or cacodylic acid. Other herbicides which may be used as the second herbicide include N-isobutyl-2-oxo-1-imidazolidinecarboxamide, aminotriazole, 2,3-dichloro-1,4-naphthoquinone, 4-amino-3,5,6-trichloropicolinic acid, N,N-dimethyl-2,2-diphenylacetamide, 2,6-dinitro-N,N-dipropyl-4-trifluoromethylaniline, N-butyl-N-ethyl-2,6-dinitro-4-trifluoromethylaniline or S,S,S-tributyl phosphorotrithioate.

The ratio of the present compound to the second herbicide may vary over a wide range according to the particular compounds involved and the intended use. In general the ratio of present compound to second herbicide lies in the range 1:0.1 to 1:15.

The present compounds may be in admixture with non-phytotoxic oils, e.g. Agri-Oil Plus or Sun Oil 11E.

In the use of the present compounds as total herbicides, high rates of application, for example at least 10 kg per hectare, such as 10–25 kg per hectare, of the compounds are usually required, unless they are mixed with other active components, in which case the rate can be reduced.

In the use of the present compounds as selective herbicides, the rate of application is usually much lower and may be for example 0.5–8 kg per hectare, such as 1–4 kg per hectare.

In the use of the compounds as plant growth regulants, low rates of application are usually required such as 0.1–4, e.g. 0.5–1, kg per hectare.

The present compounds may be applied to plants, the soil, land or aquatic areas. They are preferably used as herbicides, particularly selective herbicides, especially for selectively combating weeds by application to a locus at which a crop e.g. a food crop (particularly sugar beet), is growing or is to grow. Thus, the compounds may be applied pre- or post-planting of the crop. They may be employed for pre-emergence use or post-emergence use.

The invention is illustrated by the following Examples.

EXAMPLE 1

A solution of thionyl chloride (72 parts) in methylene chloride (270 parts) was added dropwise over a period of 30 minutes to a mixture of 2,3-dihydro-2-hydroxy-3,3-dimethyl-5-benzofuranyl methanesulphonate (130 parts) and pyridine (48 parts) in methylene chloride (1,300 parts) cooled in an ice bath. After stirring for three hours, the solution was washed twice with water, dried over sodium sulphate and the solvent distilled off under reduced pressure. The brown liquid which remained solidified to form 2-chloro-2,3-dihydro-3,3-dimethyl-5-benzofuranyl methanesulphonate (135 parts, 97% yield), melting point 59°–61° C, confirmed by its elemental analysis:

Found: C, 47.74; H, 4.74; Cl, 12.81% $C_{11}H_{13}ClO_4S$ requires: C, 47.80; H, 4.65; Cl, 12.95%

EXAMPLE 2

An attaclay/sand dust formulation of 2-chloro-2,3-dihydro-3,3-dimethyl-5-benzofuranyl methanesulphonate was incorporated into John Innes No. 1 potting compost at rates of 130 and 26 parts per million weight/volume, equivalent respectively to 56 and 11.2 kg of the compound per hectare cultivated to a depth of 50 mm. The treated soil was placed in anodised aluminium pans 200 mm long × 100 mm wide × 50 mm deep. Seeds of peas (*Pisum sativum*), mustard (*Sinapis alba*), linseed (*Linum usitatissimum*), maize (*Zea Mays*), oats (*Avena Sativa*) and ryegrass (Lolium sp.) were sown in the treated soil, one species per pan, watered and placed in a controlled environment room (temperature 22° C, relative humidity 65–85%, artificial illumination 13,000 metre-candles for 14 hours per day) for 21 days. The plants were then visually assessed for any growth regulatory or herbicidal effects, all differences from untreated controls being scored on a scale from 0 to 100 in which 0 signifies no effect and 100 signifies complete suppression. The activites against each species are tabulated below:

| Species | 130 ppm | 26 ppm |
|---|---|---|
| Peas | 95 | 65 |
| Mustard | 99 | 50 |
| Linseed | 99 | 90 |
| Maize | 98 | 90 |
| Oats | 100 | 100 |
| Ryegrass | 98 | 80 |

EXAMPLE 3

Seeds of peas (*Pisum sativum*), mustard (*Sinapis alba*), linseed (*Linum usitatissimum*), ryegrass (*Lolium* sp.), oats (*Avena sativa*) and sugarbeet (*Beta vulgaris*) were sown in anodised aluminium pans, 200 mm long × 100 mm wide × 50 mm deep containing John Innes No. 1 potting compost. They were then watered and placed in a controlled environment room (temperature 22° C, relative humidity 65–85%, artificial illumination 13,000 metre-candles for 14 hours per day). Fourteen days after sowing, the seedlings were sprayed with aqueous acetone solutions of 2-chloro-2,3-dihydro-3,3-dimethyl-5-benzofuranyl methanesulphonate at rates equivalent to 11.2 and 2.8 kg of active ingredient in 900 liters per hectare. After seven days growth in a controlled environment room the plants were visually assessed for herbicidal response, all differences from untreated controls being scored on a scale from 0 to 100 in which 0 signifies no effect and 100 signifies complete kill. The activities against each species are tabulated below.

| Species | 11.2 kg/ha | 2.8 kg/ha |
|---|---|---|
| Peas | 45 | 25 |
| Mustard | 50 | 20 |
| Linseed | 50 | 35 |
| Ryegrass | 70 | 35 |
| Oats | 60 | 40 |

| Species | 11.2 kg/ha | 2.8 kg/ha |
|---|---|---|
| Sugarbeet | 8 | 5 |

The selectivity regarding sugarbeet is apparent.

EXAMPLE 4

Seeds of wheat, barley, wild oat, blackgrass, barnyardgrass and crabgrass were sown in anodised aluminium pans 200 mm long × 100 m wide × 50 mm deep, containing John Innes No. 1 potting compost. They were then watered and placed in a controlled environment room (temperature 22°C, relative humidity 65–85%, artificial illumination 17,000 metre-candles for 14 hours per day.) Fourteen days after sowing, the seedlings were given a foliar spray of 2-chloro-2,3-dihydro,3,3-dimethyl-5-benzofuranyl methanesulphonate formulated as an aqueous acetone solution together with 500 ppm of the wetting agent Lissapol NX (Nonyl phenol/ethylene oxide condensate) at rates equivalent to 2.8, 1.4 and 0.7 kg active ingredient in 450 litres per hectare. After a further 14 days in the controlled environment room, the plants were visually assessed for any growth regulatory or herbicidal effect. All differences from an untreated control were scored on a scale 0 to 100 where 0 signifies no effect and 100 signifies complete suppression. The results are shown in the following table:

| Species | | Dosage rate kg/ha | | |
|---|---|---|---|---|
| | | 2.8 | 1.4 | 0.7 |
| Wheat | - (Triticum aestivum) | 40 | 40 | 35 |
| Barley | - (Hordeum vulgare) | 30 | 10 | 8 |
| Wild oat | - (Avena spp.) | 45 | 25 | 25 |
| Blackgrass | - (Alopecurus myosuroides) | 65 | 50 | 35 |
| Barnyardgrass | - (Echinochloa crus galli) | 65 | 60 | 60 |
| Crabgrass | - (Digitaria spp.) | 50 | 50 | 50 |

EXAMPLE 5

2-Chloro-2,3-dihydro-3,3-dimethyl-5-benzofuranyl methanesulphonate was formulated as an attaclay/sand dust and incorporated in John Innes No. 1 potting compost at a rate of 6.5 parts per million weight/volume active ingredient to soil and placed in anodised aluminium pans 200 mm long × 100 mm wide × 50 mm high. This rate is approximately equivalent to 2.8 kg of the compound per hectare cultivated to a depth of 50 mm. Seeds of the species listed below were sown in the treated soil, one species per pan, watered and placed in a controlled environment room (temperature 22° C, relative humidity 65–85%, artificial illumination 17,000 metre-candles for 14 hours per day) for 21 days. The plants were then visually assessed for any growth regulatory or herbicidal effects. All differences from an untreated control were scored on a scale from 0 to 100, where 0 signifies no effect and 100 signifies complete suppression. The activity against each species is shown below:

| Chickweed | - (Stellaria media) | 99 |
|---|---|---|
| Mustard | - (Sinapis alba) | 55 |
| Cotton | - (Gossypium sp.) | 35 |
| Tomato | - (Lycopersicon esculentum) | 75 |
| Fathen | - (Chemopodium album) | 93 |
| Carrot | - (Daucus carota) | 45 |
| Sugarbeet | - (Beta vulgaris) | 15 |
| Wheat | - (Triticum aestivum) | 99 |
| Barley | - (Hordeum vulgare) | 99 |
| Wild oat | - (Avena spp.) | 92 |
| Blackgrass | - Alopecurus myosuroides) | 98 |
| Barnyardgrass | - (Echinochloa crus galli) | 80 |
| Crabgrass | - (Digitaria sanguinalis) | 98 |

These results show a high degree of selectivity in sugarbeet.

EXAMPLE 6

A solution of thionyl bromide (26g) in methylene chloride (50 ml) was added dropwise over a period of 30 minutes to a mixture of 2,3-dihydro-2-hydroxy-3,3-dimethyl-5-benzofuranyl methanesulphonate (26g) and pyridine (10g) in methylene chloride (120ml) cooled in an ice bath. After stirring for 3hours, the solution was washed twice with water, dried over sodium sulphate and the solvent distilled off under reduced pressure. The orange gum formed was taken up in ether and filtered. The filtrate was evaporated to give an orange gum (20g) whose nuclear magnetic resonance spectrum, particularly the peak at 3.35 ppm (relative to tetramethylsilane at 10 ppm), confirmed that it was 2-bromo-2,3-dihydro-3,3-dimethyl-5-benzofuranyl methanesulphonate, purity about 80%.

I claim:

1. A plant physiologically active composition consisting essentially of an effective herbicidal or plant gowth regulating amount of a compound of the formula:

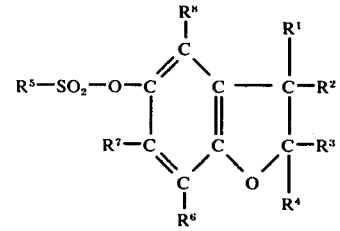

in which $R^1$, $R^2$ and $R^3$ are the same or different and each represents hydrogen or alkyl of 1–6 carbon atoms, or $R^1$ and $R^2$ together or $R^2$ and $R^3$ together form an alkylene chain of 2–5 carbon atoms;

$R^4$ represents a halogen atom;

$R^5$ represents alkyl of 1–4 carbon atoms, alkyl of 1–4 carbon atoms substituted by halogen or alkoxy of 1–6 carbon atoms, phenyl or phenyl substituted by halogen or alkyl of 1–4 carbon atoms; and $R^6$, $R^7$ and $R^8$ are the same or different and each represents hydrogen, alkyl of 1–4 carbon atoms, halogen, cyano, alkanoyl of 2–6 carbon atoms or alkoxy of 1–4 carbon atoms, together with at least one material selected from the group consisting of carriers, surface active agents, pesticides and other plant growth regulants.

2. A composition according to claim 1, wherein in the formula $R^1$ and $R^2$ are the same or different and each represents alkyl of 1–6 carbon atoms.

3. A composition as in claim 1, wherein in the formula $R^1$ and $R^2$ each represent methyl.

4. A composition according to claim 1, wherein in the formula $R^3$ represents a hydrogen atom.

5. A composition according to claim 1, wherein in the formula $R^4$ represents a chlorine atom.

6. A composition according to claim 1, wherein in the formula $R^6$, $R^7$ and $R^8$ each represent a hydrogen atom.

7. A composition according to claim 1 wherein in the formula $R^5$ represents an alkyl of 1-4 carbon atoms.

8. A composition according to claim 1, wherein in the formula $R^5$ represents methyl.

9. A composition according to claim 1, wherein the compound designated by the formula is 2-chloro-2,3-dihydro-3,3-dimethyl-5-benzofuranylmethane-sulphonate.

10. A composition according to claim 1, wherein the compound designated by the formula is 2-bromo-2,3-dihydro-3,3-dimethyl-5-benzofuranylmethane-sulphonate.

11. A composition according to claim 1 which contains a surface active agent.

12. A composition according to claim 1 which is solid and which contains a solid carrier.

13. A composition according to claim 1 which is liquid and which contains a liquid carrier which is a hydrocarbon which boils within the range 130°-270° C.

14. A composition according to claim 1 which contains a pesticide or another plant growth regulant.

15. A composition according to claim 14 which contains another herbicide.

16. A method of combating weeds at a locus infested or liable to be infested by them, which method comprises applying to the locus a weed-combating amount of a compound of the formula:

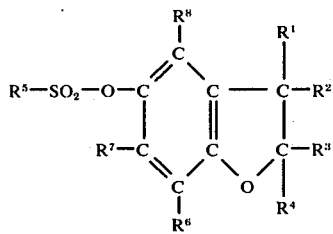

in which $R^1$, $R^2$ and $R^3$ are the same or different and each represents hydrogen or alkyl of 1-6 carbon atoms, or $R^1$ and $R^2$ together or $R^2$ and $R^3$ together form an alkylene chain of 2-5 carbon atoms;

$R^4$ represents a halogen atom;

$R^5$ represents alkyl of 1-4 carbon atoms, alkyl of 1-4 carbon atoms substituted by halogen or alkoxy of 1-6 carbon atoms, phenyl or phenyl substituted by halogen or alkyl of 1-4 carbon atoms; and $R^6$, $R^7$ and $R^8$ are the same or different and each represents hydrogen, alkyl of 1-4 carbon atoms, halogen, cyano, alkanoyl of 2-6 carbon atoms or alkoxy of 1-4 carbon atoms.

17. A method accordng to claim 16, wherein weeds are selectively combated by applying the compound to a locus at which a crop is growing or is to grow.

18. A method according to claim 16, wherein weeds are selectively combated by applying the compound to a locus at which a food crop is growing.

19. A method according to claim 16, wherein 0.5-8 kg of the compound are applied per hectare.

20. A method of regulating the growth of a plant, which method comprises applying to the locus at which the plant is growing or is to grow a plant growth regulant amount of a compound claimed in claim 16.

21. A method according to claim 16, wherein in the formula $R^1$ and $R^2$ are the same or different and each represents alkyl of 1-6 carbon atoms.

22. A method according to claim 16, wherein in the formula $R^1$ and $R^2$ each represent methyl.

23. A method according to claim 16 wherein in the formula $R^3$ represents a hydrogen atom.

24. A method according to claim 16, wherein in the formula $R^4$ represents a chlorine atom.

25. A method according to claim 16, wherein in the formula $R^6$, $R^7$ and $R^8$ each represent a hydrogen atom.

26. A method according to claim 16, wherein in the formula $R^5$ represents an alkyl of 1-4 carbon atoms.

27. A method accoridng to claim 16, wherein in the formula $R^5$ represents methyl.

28. A method according to claim 16, wherein the compound designated by the formula is 2-chloro-2,3-dihydro-3,3-dimethyl-5-benzofuranylmethane-sulphonate.

29. A method according to claim 16, wherein the compound designated by the formula is 2-bromo-2,3-dihydro-3,3-dimethyl-5-benzofuranylmethane-sulphonate.

* * * * *